United States Patent [19]
Yabe et al.

[11] Patent Number: 5,630,787
[45] Date of Patent: May 20, 1997

[54] SYSTEM INCLUDING ENDOSCOPE AND DISPOSABLE PROTECTION COVER WITH CHANNEL

[75] Inventors: Hisao Yabe, Hachioji; Yoshihiro Iida, Tama; Akira Suzuki; Hideo Ito, both of Hachioji; Yoshio Tashiro, Hino; Minoru Yamazaki; Osamu Tamada, both of Hachioji; Naruto Shinkai, Tokyo, all of Japan

[73] Assignee: Olympus Optical Co., Ltd., Tokyo, Japan

[21] Appl. No.: 37,402

[22] Filed: Mar. 26, 1993

[30] Foreign Application Priority Data

Feb. 18, 1993 [JP] Japan ................. 5-005216 U
Feb. 18, 1993 [JP] Japan ................. 5-029070
Feb. 18, 1993 [JP] Japan ................. 5-029071

[51] Int. Cl.⁶ .................................................. A61B 1/04
[52] U.S. Cl. .......................... 600/121; 600/122; 600/123; 600/153; 600/154
[58] Field of Search ........................ 128/4, 6; 600/121, 600/122, 123, 125, 153, 154, 156, 158

[56] References Cited

U.S. PATENT DOCUMENTS

| | | |
|---|---|---|
| 3,035,691 | 5/1962 | Rasmussen et al. . |
| 3,633,758 | 1/1972 | Morse . |
| 4,108,211 | 8/1978 | Tanaka . |
| 4,216,767 | 8/1980 | Aoshiro ................. 128/6 |

(List continued on next page.)

FOREIGN PATENT DOCUMENTS

| | | |
|---|---|---|
| 0341719A1 | 11/1989 | European Pat. Off. . |
| 0349479A1 | 1/1990 | European Pat. Off. . |
| 2805298A1 | 8/1978 | Germany . |
| 376128B2 | 10/1989 | Japan . |
| 3264037A | 11/1991 | Japan . |
| 4325138 | 11/1992 | Japan . |

Primary Examiner—Richard J. Apley
Assistant Examiner—Beverly M. Fanagan
Attorney, Agent, or Firm—Watson Cole Stevens Davis, P.L.L.C.

[57] ABSTRACT

An endoscope system for use in an endoscopic procedure including a plurality of endoscopes each having an insertion section to be inserted into a cavity under inspection and an operation section to which the insertion section is connected, and a plurality of disposable protection covers each having an insertion section cover for covering said insertion section of the endoscope and an operation section cover for covering said operation section of the endoscope. The operation section of the endoscope is provided with angle knobs for bending a distal end of the insertion section into a desired direction and said angle knobs are detachably secured to a shaft. In said operation section cover, there is formed an aperture through which said shaft is protruded from the operation section cover. All the angle knobs and shafts of all the endoscopes are constructed such that all the angle knobs can be detachably secured to any of the shafts.

7 Claims, 17 Drawing Sheets

U.S. PATENT DOCUMENTS

| | | |
|---|---|---|
| 4,288,882 | 9/1981 | Takeuchi . |
| 4,366,901 | 1/1983 | Short . |
| 4,404,963 | 9/1983 | Kohri . |
| 4,646,722 | 3/1987 | Silverstein et al. . |
| 4,715,360 | 12/1987 | Akui et al. . |
| 4,721,097 | 1/1988 | D'Amelio . |
| 4,741,326 | 5/1988 | Sidall et al. . |
| 4,779,727 | 10/1988 | Taterka et al. . |
| 4,825,850 | 5/1989 | Opie et al. . |
| 4,858,001 | 8/1989 | Milbank et al. . |
| 4,869,238 | 9/1989 | Opie et al. . |
| 4,877,033 | 10/1989 | Seitz . |
| 4,878,485 | 11/1989 | Adair . |
| 4,907,395 | 3/1990 | Opie et al. . |
| 4,947,827 | 8/1990 | Opie et al. . |
| 4,991,564 | 2/1991 | Takahashi et al. . |
| 4,991,565 | 2/1991 | Takahashi et al. . |
| 5,025,778 | 6/1991 | Silverstein et al. . |
| 5,042,112 | 8/1991 | Dunklee . |
| 5,050,585 | 9/1991 | Takahashi . |
| 5,105,942 | 4/1992 | van Veen et al. . |
| 5,131,537 | 7/1992 | Gonzales . |
| 5,198,894 | 3/1993 | Hicks . |
| 5,201,908 | 4/1993 | Jones ............ 128/4 |
| 5,217,001 | 6/1993 | Nakao et al. . |
| 5,237,984 | 8/1993 | Williams, III et al. . |
| 5,257,617 | 11/1993 | Takahashi . |
| 5,301,657 | 4/1994 | Lafferty et al. . |
| 5,334,142 | 8/1994 | Paradis . |
| 5,359,991 | 11/1994 | Takahashi et al. ............ 128/4 |
| 5,363,843 | 11/1994 | Daneshvar ............ 128/4 X |
| 5,419,311 | 5/1995 | Vabe et al. ............ 128/4 |

FIG_1

FIG_3
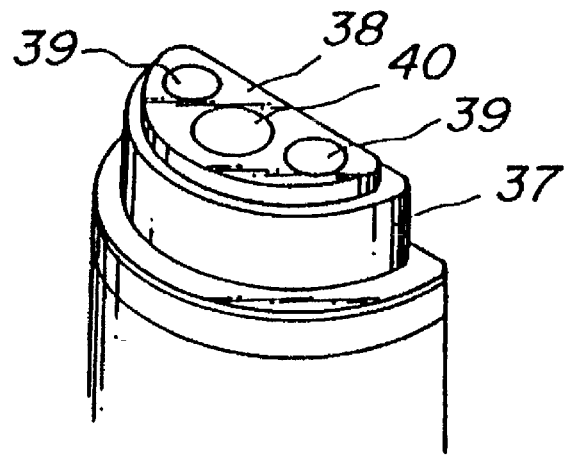
FIG_4
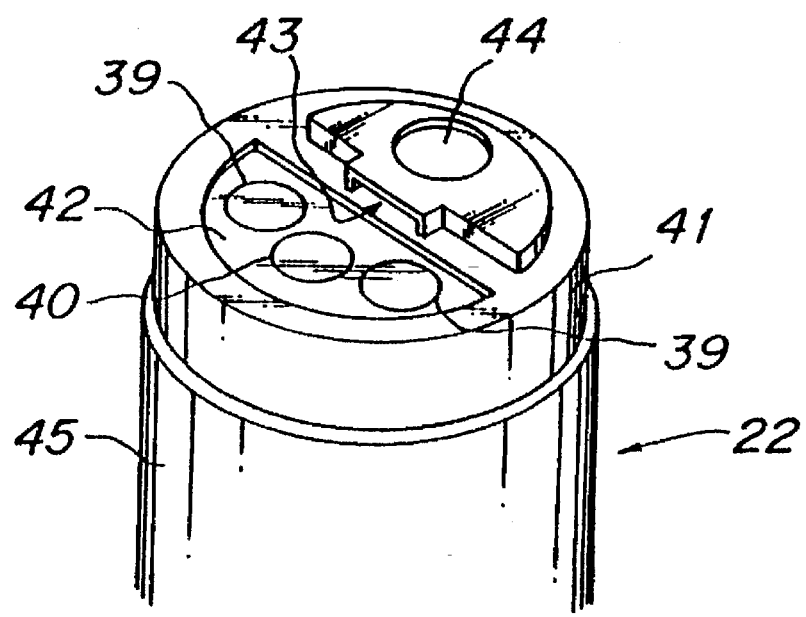

FIG_6
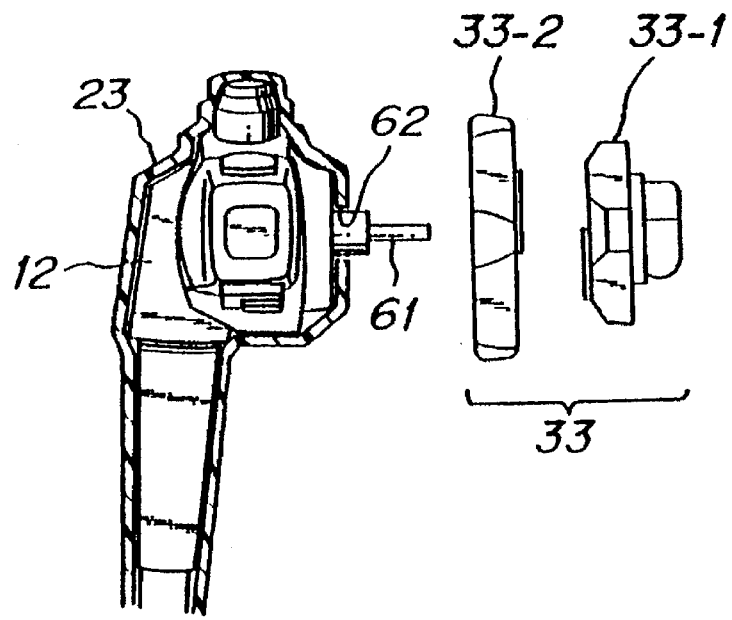
FIG_7
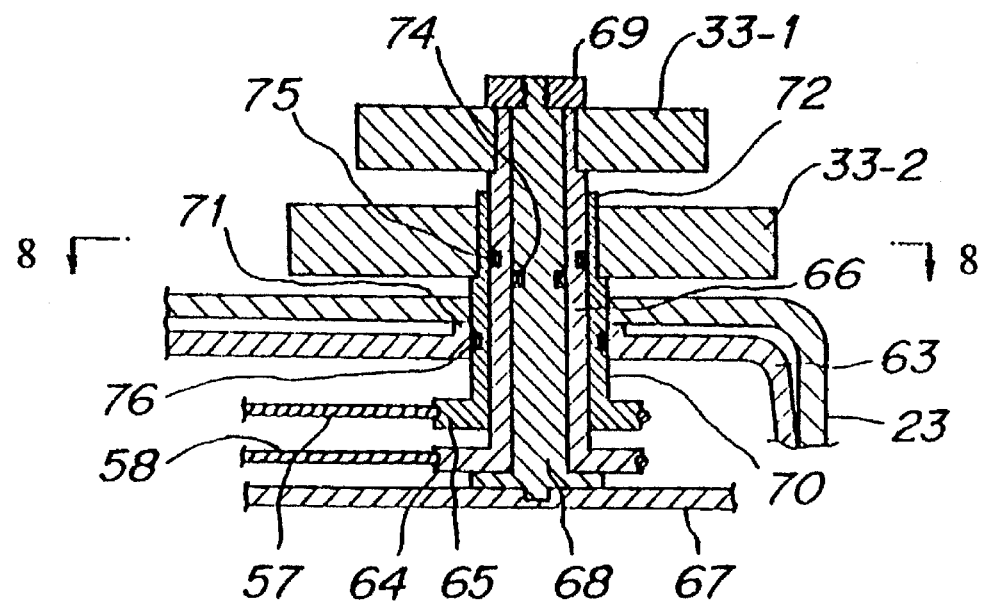

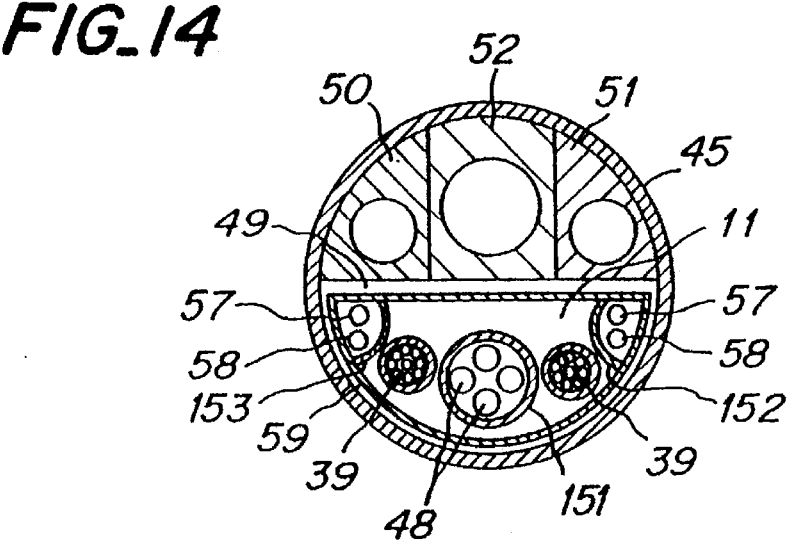
FIG_14
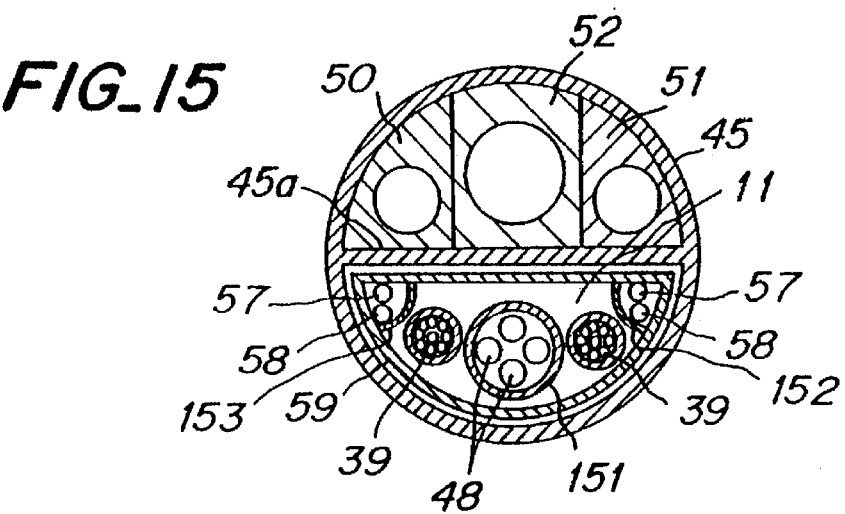
FIG_15
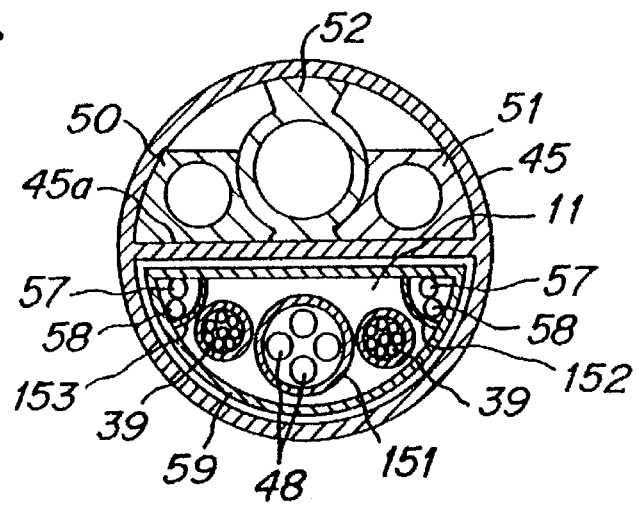
FIG_16

FIG_17
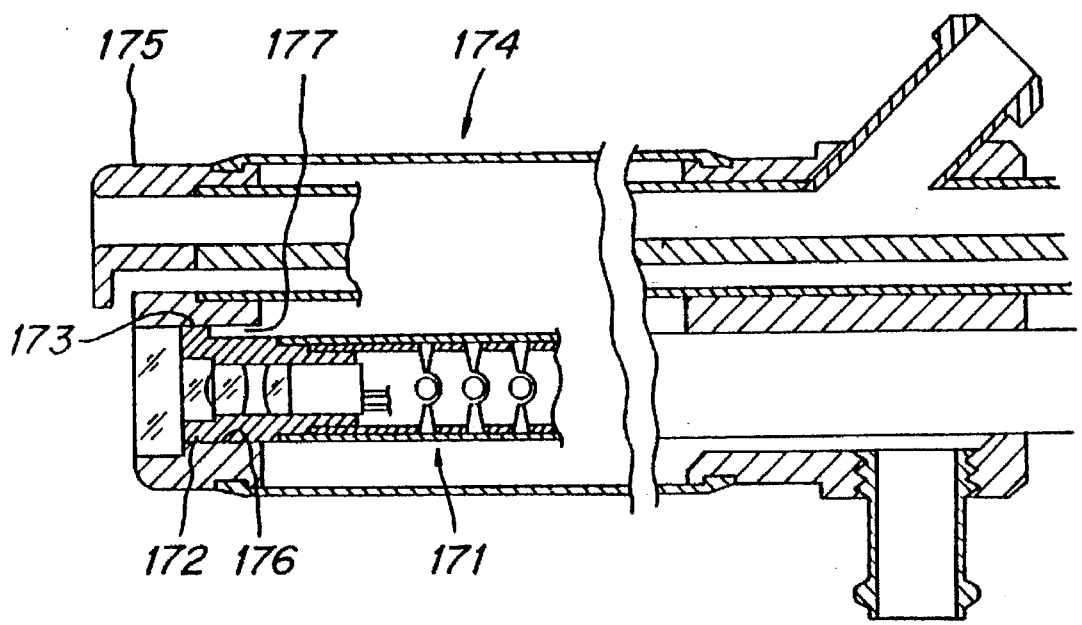

FIG_18
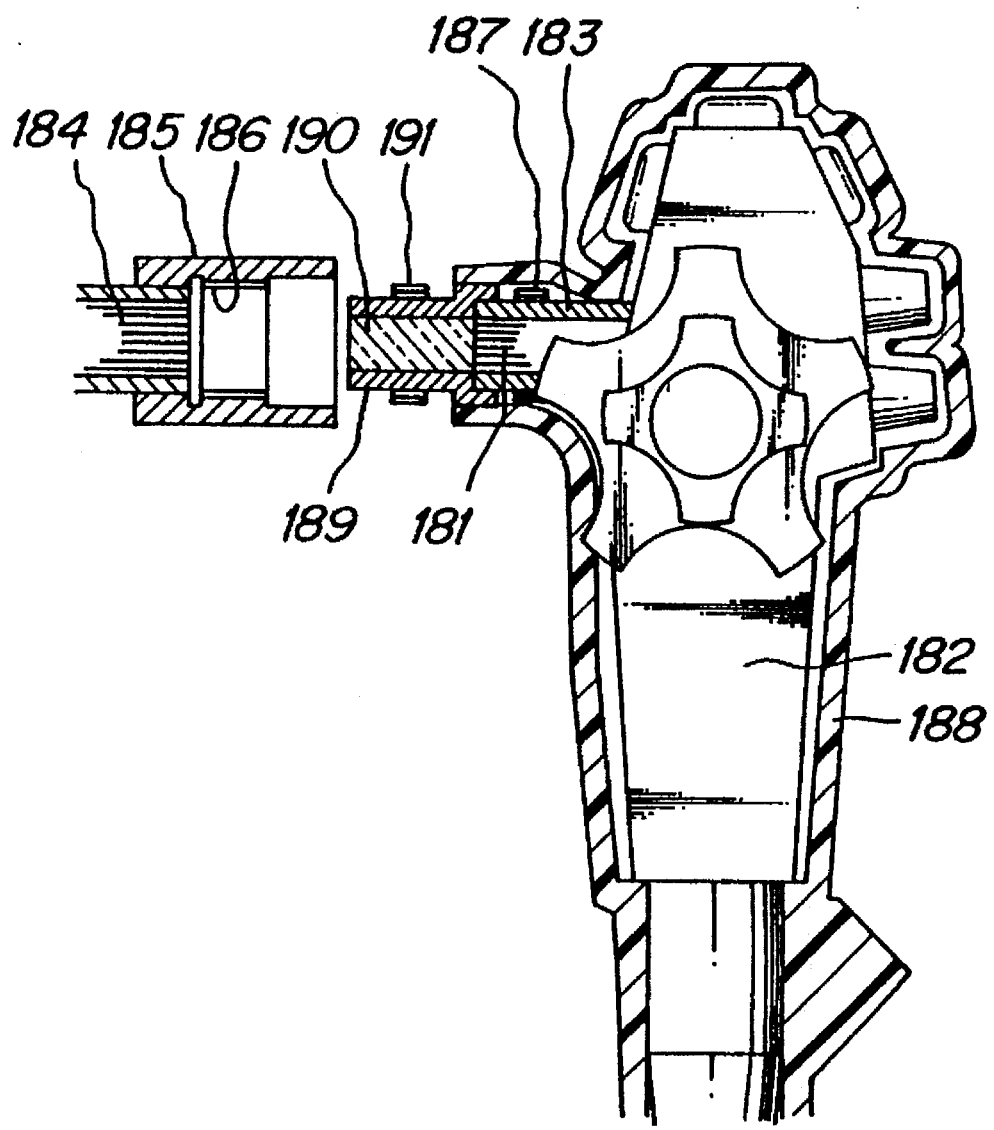

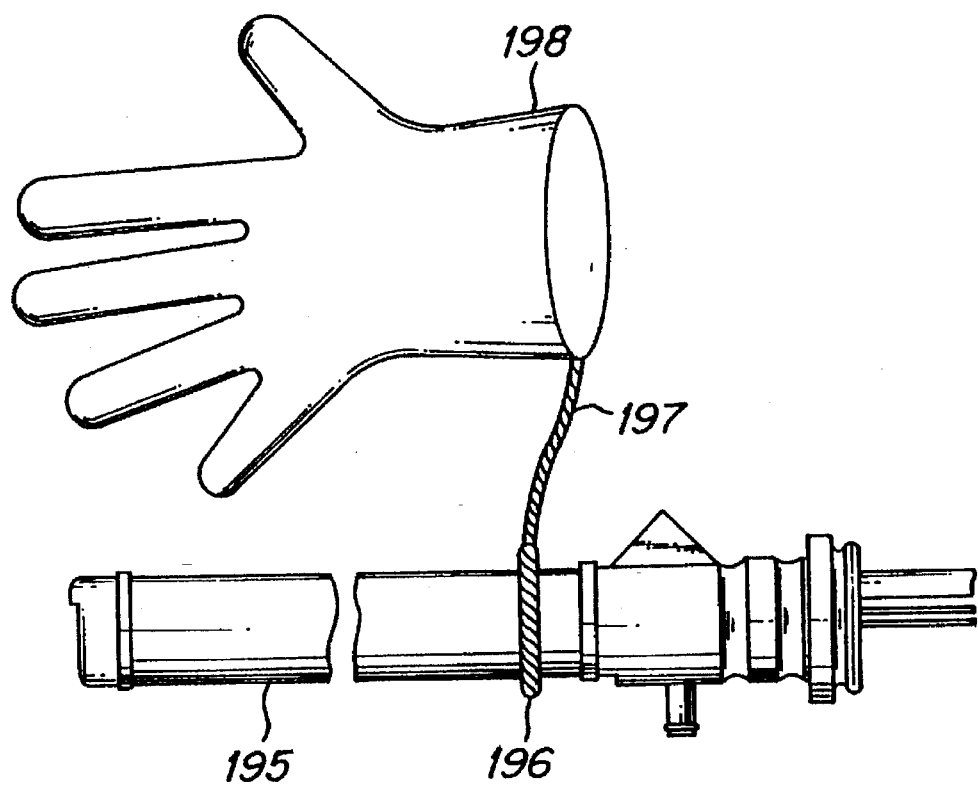

FIG_22

SYSTEM INCLUDING ENDOSCOPE AND DISPOSABLE PROTECTION COVER WITH CHANNEL

BACKGROUND OF THE INVENTION

1. Field of the Invention

The present invention generally relates to a system including an endoscope having an insertion section to be inserted into a cavity under inspection and an operation section to which a proximal end of the insertion section is connected, and a disposable protection cover having an insertion section cover for covering the insertion section of the endoscope, an operation section cover for covering the operation section of the endoscope, and at least one conduit channel extending within the insertion section cover.

2. Description of the Related Art

An endoscope system has been widely utilized for providing diagnostic and therapeutic indications for coeliac cavities of patients and for internal inspection of mechanical structures. To this end, various kinds of endoscopes have been developed. For instance, in order to inspect or treat the oesophagus, stomach and duodenum, upper endoscopes have been utilized. Further, colonoscopes have been developed to examine colons, and sigmoidoscopes have been proposed to inspect rectums and sigmoid colons. When the endoscope is used, an insertion portion of the endoscope has to be inserted into a cavity of a patient, so that the outer surface of the insertion section of the endoscope becomes contaminated with living tissues and liquids. Such a contaminated endoscope can not be successively used for patients. Therefore, once the endoscope is used to diagnose and/or treat a patient, it is necessary to clean and sterilize the endoscope. Of course, the cleaning of the endoscope requires a substantial amount of time, and during this cleaning time, it is impossible to perform endoscopic procedures using this endoscope. In order to mitigate such an idle time, it is necessary to prepare a large number of endoscopes. However, endoscopes are rather expensive, so that it is practically difficult to prepare a large number of endoscopes, particularly in a small hospital or clinic. Therefore, in almost all hospitals and clinics, in practice, after the endoscope has been used for examining or treating a patient, the endoscope is immediately cleaned. Typically, this cleaning requires several minutes to ten minutes. In order to effect the complete washing and sterilization, the cleaning has be to performed for several tens of minutes.

Further, the endoscope has various channels such as an air channel, a water channel, a suction channel, and a forceps channel which extend along the insertion section from a proximal end to a distal end thereof, and these channels, except the forceps channel, are connected via tubes to respective devices such as an air supply pump, a water supply pump, a water suction pump and an air suction pump. These channels are subjected to contact with living tissues and liquids. However, in order to clean these channels of the endoscope completely, a relatively long time is required. Thus, the endoscope can not be utilized efficiently for the long cleaning time. In a large hospital or clinics, a large number of endoscopes may be prepared in order to mitigate the problem of cleaning time. However, this solution results in an increase in operating costs. Further, in small clinics, it is practically impossible to prepare a number of expensive endoscopes.

Moreover, the endoscope might be broken during cleaning and the usable life of the endoscope is liable to be shortened by the cleaning.

In order to avoid the above-explained various problems, there has been proposed an endoscope system, in which the endoscope is covered with a disposable protection sheath-like cover having channels formed therein. For instance, U.S. Pat. Nos. 4,721,097, 4,741,326, 4,825,850, 4,869,238, 4,991,564, 4,991,565, 5,050,585 disclose various kinds of disposable protection sheath-like covers having channels formed therein. In U.S. Pat. No. 4,646,722, there is shown an endoscope system in which the endoscope is covered with a protection sheath, while a tube having channels formed therein is inserted into a U-shaped cutout formed in an outer surface of the endoscope along a longitudinal axis thereof. Upon diagnosis, the insertion section of the endoscope is covered with the protection sheath, and after the inspection, the sheath is removed from the insertion section and is then discarded. Therefore, it is no longer necessary to clean the endoscope after every inspection.

In the above-mentioned U.S. Patents, the protection sheath-like cover is constructed to cover only the insertion section of the endoscope, but does not cover an operation section of the endoscope. It should be noted that the operation section of the endoscope is handled by doctors and operators, and thus is brought into contact with the living tissues and liquids of a patient. Therefore, in order to remove the contamination of the operation section of the endoscope due to such living tissues and liquids, it is advantageous to cover not only the insertion section, but also the operation section of the endoscope.

In European Patent Publication No. 0 349 479 A1, there is disclosed an endoscope system, in which not only the insertion section, but also the operation section of the endoscope are covered with a disposable protection cover. That is to say, the protection cover comprises a sheath-like portion for covering the insertion section of the endoscope and a bag-like portion for covering the operation section, the sheath-like portion and bag-like portion being integrally formed. The operation section of the endoscope is usually provided with various operating members such as angle knobs and optical system adjusting members. The endoscope shown in the above mentioned European Patent Publication No. 0 349 479 A1 is of a colonoscope type, so that angle knobs are not provided. However, a focus adjusting ring is provided, which has to be operated during the inspection. To this end, an aperture is formed in the bag-like portion of the protection cover at a position corresponding to the focus adjusting ring. In this case, in order to operate the ring easily, it is preferable to form a large aperture. However, contamination via the aperture is liable to be large.

In order to avoid such a drawback, in European Patent Publication No. 0 341 719 A1, there is proposed another known endoscope system, in which an insertion section of an endoscope is covered with a disposable protection sheath-like cover, and an operation section of the endoscope is covered with a disposable protection bag-like cover which is mated or joined with the protection sheath-like cover in order to prevent contamination through the junction of the sheath-like cover and the bag-like cover. In this known endoscope system, angle knobs are detachably secured to a shaft extending from a housing of the operation section. The shaft protrudes from the protection bag-like cover through an aperture formed therein. Since a diameter of the shaft is much smaller than a diameter of the angle knobs, a size of the aperture can be made much smaller than the angle knobs. Therefore, a possibility of contamination via the aperture formed in the bag-like cover can be reduced as compared with a case in which a large aperture, through which the angle knobs are projected from the bag-like cover, is formed in the bag-like cover.

However, in typical endoscopes, angle knobs for moving the distal end of the insertion section in the up and down directions as well as in the right and left directions are secured to the shaft, and it is not necessary to remove the angle knobs from the shaft during the usual usage. Therefore, in the known endoscopes, the couplings of the angle knobs with the shaft are effected in various ways, and a set of angle knobs destined for a certain endoscope can not be secured to a shaft of another endoscope. In the usual endoscopes, this does not cause any problem, because the angle knobs and shaft are not usually decoupled from each other. However, in the endoscope system disclosed in the above-cited European Patent Publication No. 0 341 719 A1, this results in a serious problem. In an endoscopic procedure area, various different types of endoscopes are arranged, and therefore, once the angle knobs are removed from the shaft extending from the operation section of the endoscope, it is not easy for users to select the correct angle knobs. If angle knobs which are not mated with a shaft of an operation section of a particular endoscope are forcibly secured to this shaft, the angle knobs and/or shaft might be broken.

In a system including an endoscope and a disposable protection cover, if a pin hole is formed in the sheath-like cover, contamination arises via the pin hole. In order to avoid such a problem, respective protection sheath-like covers have to be checked in a factory, and only sheath-like covers which have been checked to have no pin hole are shipped or forwarded. However, the known sheath-like covers are not formed such that such a pin hole check can be performed easily, so that in practice, pin hole checking has not been performed. Therefore, there is a danger that a protection sheath-like cover having a pin hole will be used for the endoscopic procedure. Therefore, it is preferable to effect the pin hole check at the factory as well as at the endoscopic procedure site in a positive and easy manner. However, in the known system disclosed in the above-mentioned prior art references, this pin hole check can not be carried out easily.

Further, in known endoscope systems using disposable protection sheath-like covers, various conduit channels are provided within the cover. In practice, these conduit channels are formed by flexible tubes, and these tubes are extended within the cover from a proximal end to a distal end thereof. At these proximal and distal ends, these tubes are fixed to construction members made of rather rigid material so that they can assume predetermined positions at these ends. However, substantial portions of the tubes except for the proximal and distal ends thereof are not fixed, but are extended freely. Usually these tubes have a circular cross section, and thus relatively large spaces are formed between these tubes. Therefore, when the insertion section is bent by suitably operating the angle knobs, one or more tubes might move relatively largely. Then, the tubes might resist the smooth bending movement of the insertion section, and the distal end of the insertion section might not be directed in a desired direction, but might be bent in a direction which is different from the desired direction. As is readily apparent, this causes a problem in handling the endoscope during the inspection.

SUMMARY OF THE INVENTION

The present invention has for its object to provide a novel and useful endoscope system including an endoscope having an operation section, an insertion section extending from the operation section and angle knobs provided on the operating section; and a protection cover for covering the operation section and insertion section, in which a doctor or operator can easily couple the angle knobs with a shaft protruding from a housing of the operation section via an aperture formed in a portion of the cover covering at least the operation section of the endoscope.

It is another object of the invention to provide a novel and useful protection cover for covering at least an insertion section of an endoscope, in which a pin hole check for the protection cover can be performed easily.

It is another object of the instant invention to provide a novel and useful protection cover for covering at least an insertion section of an endoscope and having at least one conduit channel, in which a distal end of the insertion section of the endoscope covered with the protection cover can be correctly bent in a desired direction without being affected by the movement of the conduit channel within the cover.

It is still another object of the present invention to provide a novel and useful endoscope which can be advantageously used for the above-mentioned novel and useful endoscope system.

According to a first aspect of the invention, in an endoscope system including a plurality of endoscopes each having an operation section having a housing, a shaft extending from the housing and at least one angle knob detachably secured to the shaft and an insertion section extending from the operation section and being insertable into a cavity to be examined, and a plurality of protection covers each for covering at least the operation section of an endoscope, the protection cover having an aperture through which the shaft of the endoscope is protruded from the protection cover when the endoscope is covered with the protection cover, the improvement being characterized in that the shafts and angle knobs of the plurality of endoscopes are constructed such that each of the angle knobs of the plurality of endoscopes can be commonly used for respective shafts of the plurality of endoscopes.

In the endoscope system according to the invention, each of the angle knobs can be detachably secured to a shaft of any endoscope, so that it is no longer necessary to select a suitable angle knob among a plurality of angle knobs decoupled from the endoscopes. Therefore, the preparatory operation of doctors or operators can be made very simple and the damage of the angle knobs and/or shafts can be prevented effectively. According to a second aspect of the invention, in a protection cover for use in an endoscope having an operation section and an insertion section extending from the operation section, the protection cover being formed to cover at least the insertion section of the endoscope, the improvement being characterized in that the protection cover comprises an insertion section cover for covering the insertion section of the endoscope and a connecting portion secured to a proximal end of the insertion section cover, and a pin hole checking opening formed in the connecting portion, wherein through the pin hole checking opening a fluid can be supplied into the insertion section cover such that a pin hole formed in the insertion section cover can be checked.

In the above-mentioned protection cover according to the invention, any pin hole formed in the insertion section cover can be easily checked by introducing a fluid such as air and liquid into the insertion section cover before shipment or just before the usage of the endoscope at the endoscopic procedure site. Therefore, any undesired contamination via a possible pin hole can be effectively prevented.

According to a third aspect of the invention, in a protection cover for covering at least an insertion section of an endoscope and having at least one flexible conduit channel extending within the protection cover from a proximal end to a distal end thereof, the improvement being characterized in that the protection cover is constructed such that the conduit channel is prevented from moving freely in a radial direction thereof within the protection cover.

In such a protection cover according to the invention, the movement of the conduit channel in the radial direction within the cover is effectively prevented, so that the conduit channel does not prevent the smooth movement of the distal end of the insertion section of the endoscope. Therefore, the distal end of the insertion section can be directed into a desired direction by operating the angle knobs.

BRIEF DESCRIPTION OF THE DRAWINGS

FIG. 3 is a perspective view depicting the distal end of the insertion section of the endoscope;

FIG. 4 is a perspective view illustrating the construction of the distal end of the insertion section cover;

FIG. 6 is a longitudinal cross sectional view depicting the construction of the operation section of the endoscope;

FIG. 7 is a cross sectional view representing the detailed construction of the shaft of the operation section;

FIG. 14 is a cross sectional view depicting the construction of the insertion section cover according to the invention;

FIG. 15 is a cross sectional view showing another embodiment of the insertion section cover according to the invention;

FIG. 16 is a cross sectional view illustrating still another embodiment of the insertion section cover according to the invention;

FIG. 17 is a cross sectional view showing another embodiment of the endoscope system according to the invention;

FIG. 18 is a cross sectional view illustrating another embodiment of the operation section cover according to the invention;

FIG. 19 is a side view depicting another embodiment of the insertion section cover according to the invention;

EXPLANATION OF THE PREFERRED EMBODIMENTS

Figure 1:
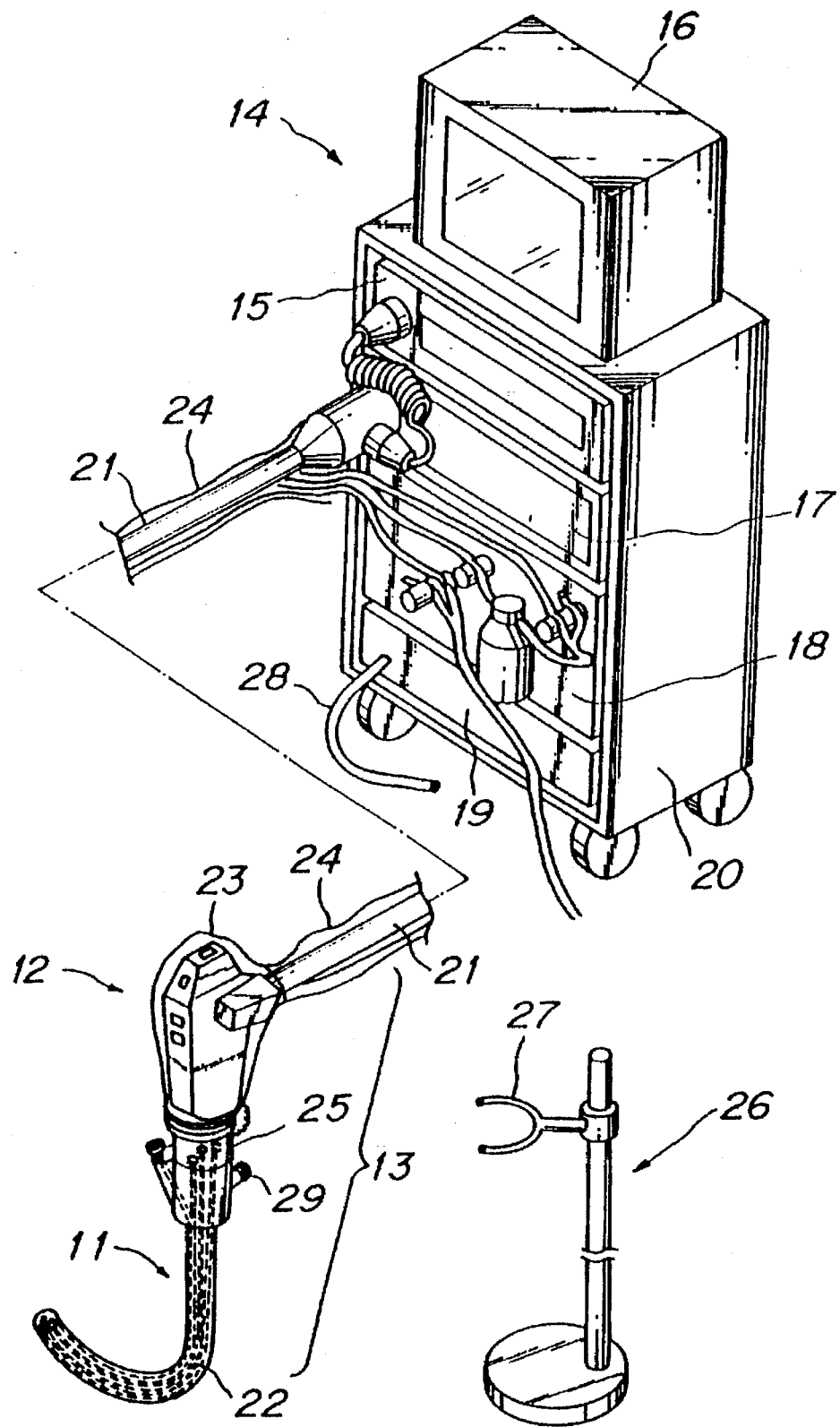
FIG. 1 is a perspective view showing the whole construction of an embodiment of the endoscope system according to the invention.

FIG. 1 is a schematic view showing an embodiment of the endoscope system according to the invention including an endoscope apparatus and a disposable protection cover. The endoscope apparatus comprises an endoscope 13 having an insertion section 11 and an operation section 12 with which a proximal end of the insertion section is coupled, and an external apparatus 14 coupled with the endoscope 13. The external apparatus 14 comprises a video processor 15 having a circuit for driving a solid state image sensor provided within a distal end of the insertion section 11 and a circuit for processing an image signal read out of the solid state image sensor, a monitor device 16 for displaying an image of an object under inspection by processing the image signal supplied from the video processor 15, a light source device 17 for emitting light for illuminating the inside of a cavity by means of a light guide optical fiber bundle extending within the insertion section 11, a fluid control device 18 having an air pump for supplying air and a suction pump for sucking liquids, and an inflator 19 for inflating the disposable protection cover such that the insertion section 11 of the endoscope 13 can be easily inserted into and removed from the disposable protection cover as will be explained later in detail. These devices are installed in a box 20 having casters. The video processor 15 and light source device 17 are coupled with the operation section 12 of the endoscope 13 by means of signal conductors and a light guide optical fiber bundle provided in a universal cord 21, and the fluid control device 18 is coupled with the conduit channels provided within the disposable protection cover by means of conduit tubes arranged along the universal cord 21. The construction and operation of the above mentioned devices, except for the inflator 19, are well known in the art, so that detailed explanation thereof is unnecessary.

The disposable protection cover of the present embodiment comprises an insertion section cover 22 for covering the insertion section 11 of the endoscope 13, an operation section cover 23 for covering the operation section 12 of the endoscope and a universal cord cover 24 for covering the universal cord 21. These disposable protection covers 22, 23 and 24 are formed separately from each other, and suitable coupling mechanisms are provided between junctions thereof in order to avoid possible contamination through the junctions.

The protection covers 22, 23 and 24 may be made of various materials. For instance, flexible vinyl and rubber may be used as a soft material, and rigid or semi-rigid plastics may be used as a hard material. It should be noted that the protection covers 22, 23 and 24 are not always necessarily made of the same material, but may be made of different materials. For instance, the insertion section cover 22 may be made of flexible rubber, the operation section cover 23 may be made of rigid plastics and the universal cord cover 24 may be made of semi-rigid vinyl.

Prior to the actual examination, a set of protection covers is removed from a package, and a connecting portion 25, made of rigid or semi-rigid plastics and provided at a proximal end of the insertion section cover 22, is hung from a cover supporting member 27 of a cover supporting stand 26. In order to prevent the connecting portion 25 from being contaminated, the cover supporting member 27 may be covered with a disposable cover. As will be explained later, the connecting portion 25 of the insertion section cover 22 is utilized to couple the insertion section cover with the operation section cover 23.

The height of the cover supporting member 27 is adjusted such that when the insertion section cover 22 is hung from the cover supporting member 27, the distal end of the disposable insertion section cover is not brought into contact with a floor. However, if the height of the cover supporting member 27 is made too high, the inserting operation becomes difficult, so that the cover supporting member should not be made so high. In such a case, the insertion section cover 22 has to be supported by an operator.

After the insertion section cover 22 has been hung from the cover supporting member 27, an end of an air supply tube 28 connected to the inflator 19 is coupled with a nipple portion 29 provided in the connecting portion 25 of the insertion section cover 22, and then the inflator 19 is driven to supply air through the tube 28 into insertion section cover 22. In this manner, the insertion section cover 22 is inflated, so that the insertion section 11 of the endoscope 13 can be easily inserted into the insertion section cover 22. Then, the inflator 19 is de-energized, and the tube 28 is decoupled from the nipple portion 29. This inflating operation is also performed upon removing the insertion section 11 from the insertion section cover 22. After the examination, the protection covers 22, 23 and 24 are discarded as medical waste, and the endoscope is cleaned and sterilized after all examinations for one day have been finished.

Figure 2:
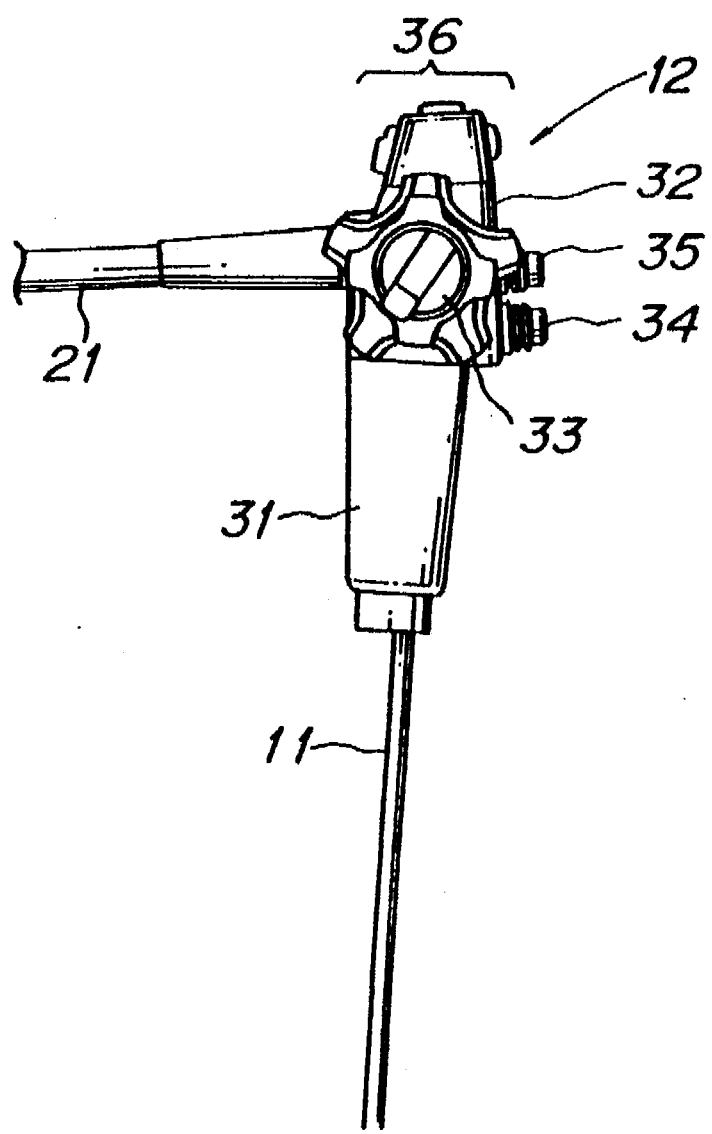
FIG. 2 is a front view illustrating the construction of the operation section of the endoscope shown in FIG. 1.

FIG. 2 shows the construction of the operation section 12 of the endoscope. The insertion section 11 and universal cord 21 are connected to the operation section 12. The operation section comprises a grip portion 31 and a main portion 32. The main portion 32 comprises angle knobs 33 for bending the distal end of the insertion section 11, air and water supply control switch 34, suction control switch 35 and function switches 36 for controlling the operation of a camera taking photographs of the object under inspection. As will be explained later, according to the present invention, the angle knobs 33 are detachably secured to the main portion 32 of the operation section 12. The angle knobs 33 may be of a disposable type and may be contained in a package in which the disposable protection cover is installed. Alternatively, the angle knobs may be reused after sterilization.

FIG. 3 is a perspective view illustrating the construction of the insertion section 11 of the endoscope. In the present embodiment, a lateral cross section of a distal end construction member 37 is semicircular and in a front surface 38 of the member 37 there are arranged outlets of a pair of illuminating optical systems, i.e. optical fiber bundles 39 and an observing optical system 40 provided between the illuminating optical systems.

Figure 5:
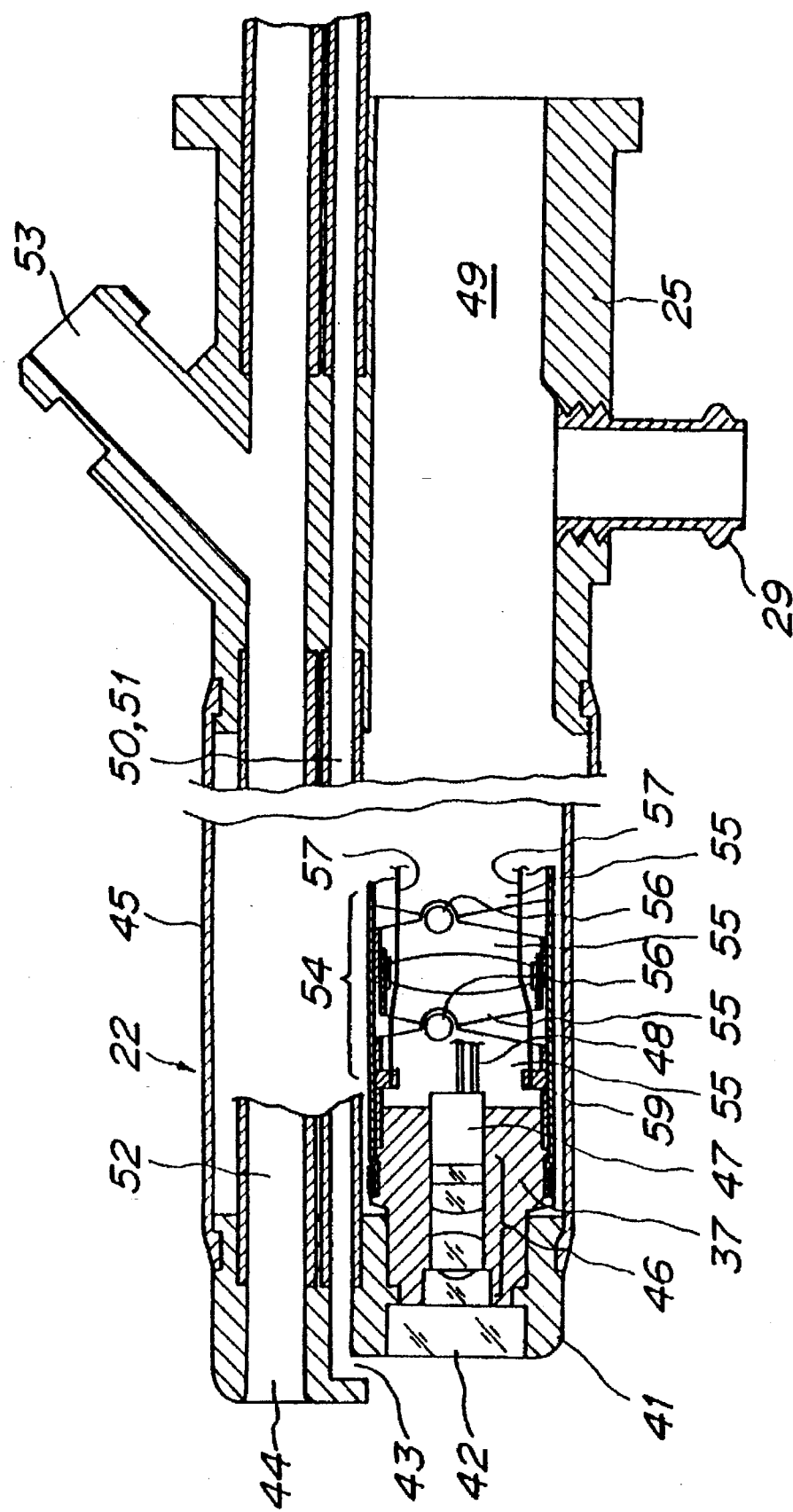
FIG. 5 is a longitudinal cross sectional view showing the endoscope system shown in FIG. 1.

FIG. 4 is a perspective view depicting the construction of a distal end of the insertion section cover 22, and FIG. 5 is a longitudinal cross sectional view showing the insertion cover 22 into which the insertion section 11 of the endoscope is inserted. In a front surface of a distal end construction member 41 of the insertion section cover 22, there are provided a semicircular observation window 42 made of transparent material, a nozzle 43 for ejecting air and water toward the window 42, and an outlet opening 44 of a forceps channel 52. By ejecting the air and water from the nozzle 43, the outer surface of the observation window 42 can be cleaned.

To the distal end construction member 41 of the insertion section cover 22 is connected one end of an insertion section cover tube 45 which isolates a main portion of the insertion section 12 from the external environment. This cover tube 45 is made of a flexible material. In the present embodiment, the cover tube 45 is made of flexible rubber. The other end of the cover tube 45 is connected to the connecting portion 25 of the insertion section cover 22.

As illustrated in FIG. 5, within the distal end construction member 37 of the insertion section 11 which faces the observation window 42 of the distal end construction member 41 of the insertion section cover 22, there are arranged an observing lens system 46 for forming an image of an object under inspection and a solid state image sensor 47 for picking-up the image of an object under inspection. The solid state image sensor 47 is electrically connected to the video processor 15 (FIG. 1) by means of signal conductors 48 extending through the insertion section 11 and universal cord 21.

Within the insertion section cover 22, there are formed: endoscope insertion channel 49 into which the insertion section 11 is inserted, air supply conduit 50 communicated with the air and water ejecting nozzle 43, water supply conduit 51 also communicated with the nozzle 43, and forceps channel 52. These channels and conduits are arranged in parallel with each other. The forceps channel 52 is communicated with a forceps inlet opening 53 provided in the connecting portion 25 and is also communicated with the fluid control device 18 by means of a conduit tube provided within the universal cord 21. Therefore, the forceps channel 52 is sometimes called a suction channel. Further, the conduits 50 and 51 are also called conduit channels or conduit tubes in the present specification.

In order to bend the distal end of the insertion section 11 by operating the angle knobs 33 such that an optical axis of the observing optical system 46 is moved up and down as well as right and left, there is provided a bending portion 54 adjacent to the distal end construction member 37 of the insertion section 11 of the endoscope. The bending portion 54 comprises a series of nodal rings 55 which are coupled with each other by means of journal pins 56, and a front end ring is connected to the distal end construction member 37 of the insertion section 11. A pair of wires 57, 58 are secured to the front end ring 55 at diametrically opposing points. These wires 57, 58 are extended within the insertion section 11 and are wound around a pair of pulleys provided in the operation section 12. In FIG. 5, only the wire 57 is shown, but the other wire 58 is illustrated in FIG. 7. A series of nodal rings 55 is covered with a flexible rubber tube 59 in a liquid tight manner. By operating the angle knobs 33, the pulleys may be rotated, and thus the wires 57, 58 may be moved so as to direct the distal end of the insertion section 11 into a desired direction. This construction is well known in the art, so that its detailed explanation is unnecessary.

FIG. 6 shows a mechanism for detachably securing the angle knobs 33 to a shaft 61 provided in the operation section 12 of the endoscope. The operation section 12 is covered with the operation section cover 23. In this operation section cover 23, there is formed an aperture 62 through which the shaft 61 is extended from the cover 23. A diameter of the aperture 62 is much smaller than a diameter of the shaft 61, so that contamination via this aperture can be reduced to a great extent. In the present embodiment, the distal end of the insertion section 11 of the endoscope may be bent right and left as well as up and down, and thus there are provided a right and left angle knob 33-1 and an up and down angle knob 33-2.

Figure 8:
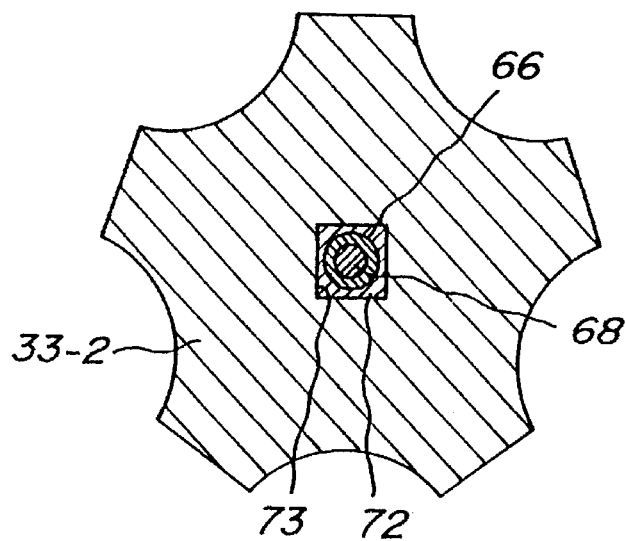
FIG. 8 is a cross sectional view cut along a line 8—8 in FIG. 7 for showing the rectangular hole formed in the angle knob.

FIG. 7 is a cross sectional view illustrating the detailed construction of the detachably securing mechanism of the angle knobs 33-1 and 33-2 to the shaft 61, and FIG. 8 is a cross sectional view cut along a line 8—8 in FIG. 7. Within a housing of the operation section 12 there are arranged the pair of pulleys 64 and 65. The lower pulley 64 is integrally formed with a base portion of a first rotary shaft 66 in the form of a cylinder, and the wire 58 is wound around the pulley 64. The first rotary shaft 66 is rotatably supported by a supporting rod 68 which is secured to a base 67 provided in the housing 63. A front end portion of the first rotary shaft 66 is protruded from the housing 63 as well as from the operation section cover 23, and the first angle knob 33-1 may be detachably secured to the thus protruded front end portion of the first rotary shaft by means of a nut 69. The second pulley 65 is formed integrally with a base portion of a second rotary shaft 70 which is rotatably provided around the first rotary shaft 66, so that the first and second rotary shafts 66 and 70 are arranged coaxially with each other. The wire 57 is wound around the second pulley 65. The end rotary shaft 70 is journaled by a bearing 71 secured to the housing 63. A front end portion of the second rotary shaft 70 is protruded from the housing 63 and operation section cover 23. In this case, the second rotary shaft 70 is extended below the lower surface of the first angle knob 33-1. As clearly shown in FIG. 8, the front end 72 of the second rotary shaft 70 is shaped to have a rectangular cross section. In a center of the second angle knob 33-2 there is formed a rectangular opening 73 corresponding to the rectangular front end 72 of the second rotary shaft 70. In this manner the second angle knob 33-2 may be detachably secured to the front end 72 of the second rotary shaft 70 by inserting the rectangular front end into the rectangular opening 73. There are further provided sealing members 74, 75 and 76 between the first rotary shaft 66 and the supporting rod 68, between the first and second rotary shafts 66 and 70, and between the second rotary shaft 70 and the bearing 71, respectively. In this manner, in the present embodiment, the supporting rod 68 and first and second rotary shafts 66 and 70 constitute the shaft 61.

Figure 9:
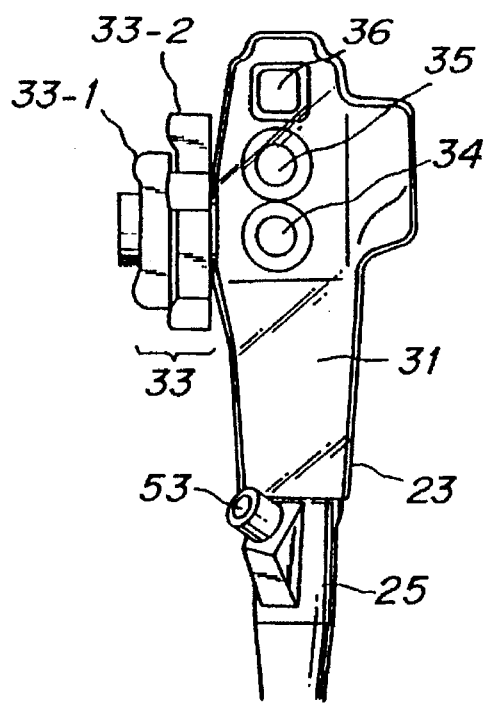
FIG. 9 is a side view showing the condition of the operation section of the electronic scope which is covered with the operation section cover.
Figure 10:
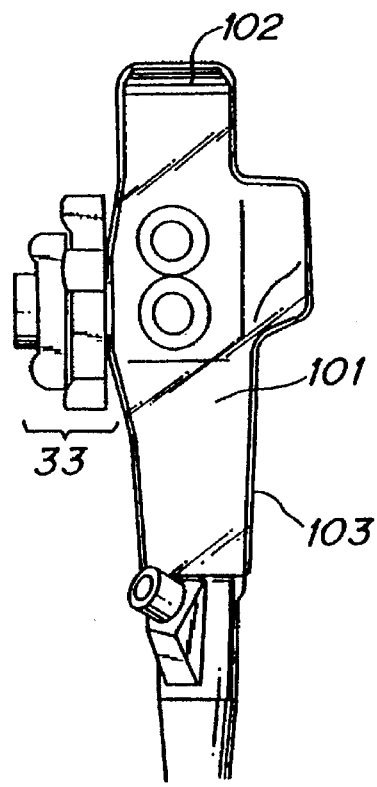
FIG. 10 is a side view illustrating the condition of the operation section of the fiber scope.

FIG. 9 illustrates the construction of the operation section 11 of the endoscope of the present embodiment. In the present embodiment, the endoscope is of the electronic scope type in which the solid state image sensor 47 (see FIG. 5) is arranged in the distal end of the insertion section 11. FIG. 10 shows an operation section 101 of another embodiment of the endoscope according to the invention. In this embodiment, the endoscope is constructed as of a fiber scope. In the operation section 101, there is provided an eyepiece portion 102 for observing the image of the object under inspection. Therefore, the shape of an operation section cover 103 for covering the operation section 101 is somewhat different from that of the insertion section cover 23 of the embodiment shown in FIG. 9, so that they can not be used commonly. However, according to the invention, the constructions of the shafts protruded from the operation section covers 23 and 103 via the apertures formed therein and the angle knobs detachably secured thereto are identical with each other, so that the angle knobs 33 can be commonly used for both endoscopes shown in FIGS. 9 and 10. In this case, if the construction of the insertion section of the electronic scope shown in FIG. 9 is identical with that of the operation section of the fiber scope, the insertion section covers may be also commonly used for both endoscopes.

Figure 11:
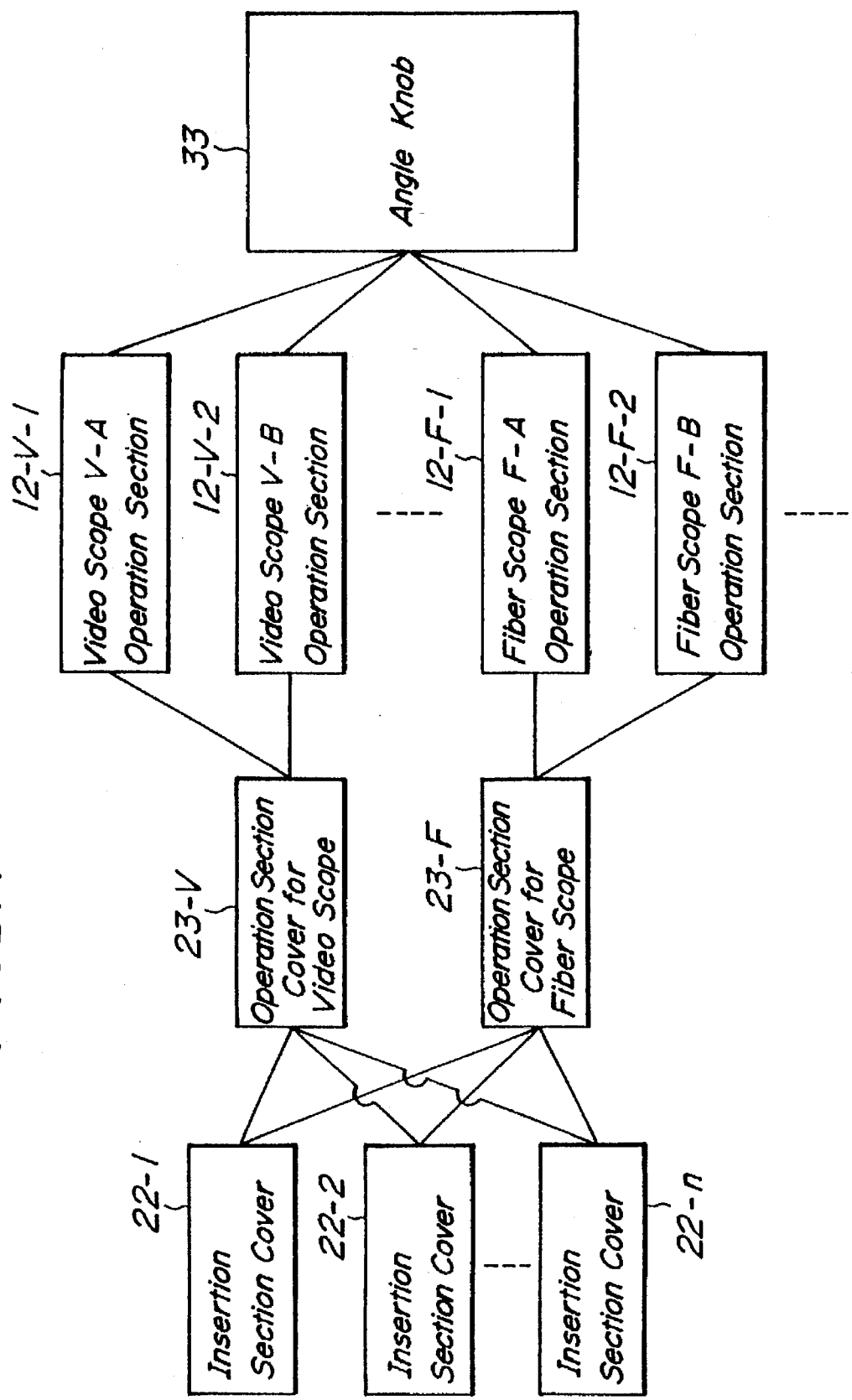
FIG. 11 is a schematic diagram representing the general construction of the endoscope system according to the invention.

FIG. 11 is a schematic view showing the general construction of the endoscope system according to the invention. In this endoscope system, there are provided a plurality of video scopes V-A, V-B—used together with disposable protection covers and a plurality of fiber scopes F-A, F-b—used together with disposable protection covers. According to the invention, the angle knobs 33 are constructed such that they can be commonly used for operation sections 12-V-1, 12-V-2—12-F-1, 12-F-2—of all the endoscopes. Therefore, it is no longer necessary to select angle knobs in dependence upon an endoscope to be used, so that the shafts and angle knobs are hardly damaged. Further, the operation section cover 23-V can be commonly used for various video scopes V-A, V-B—comprising insertion sections having different shapes and lengths. Similarly, the operation section cover 23-F can be commonly used for the fiber scopes comprising insertion sections having different shapes and lengths. Moreover, the insertion section covers 22-1, 22-2—22-n can be commonly used not only for the insertion sections of electronic scopes but also for the insertion sections of fiber scopes if the shape and length of the insertion sections are the same. In this manner, according to the invention, the various components can be commonly used for various endoscopes, and thus the operation for selecting the components can be made simple to a large extent, and possible damage due to erroneous selections can be prevented.

Figure 12:
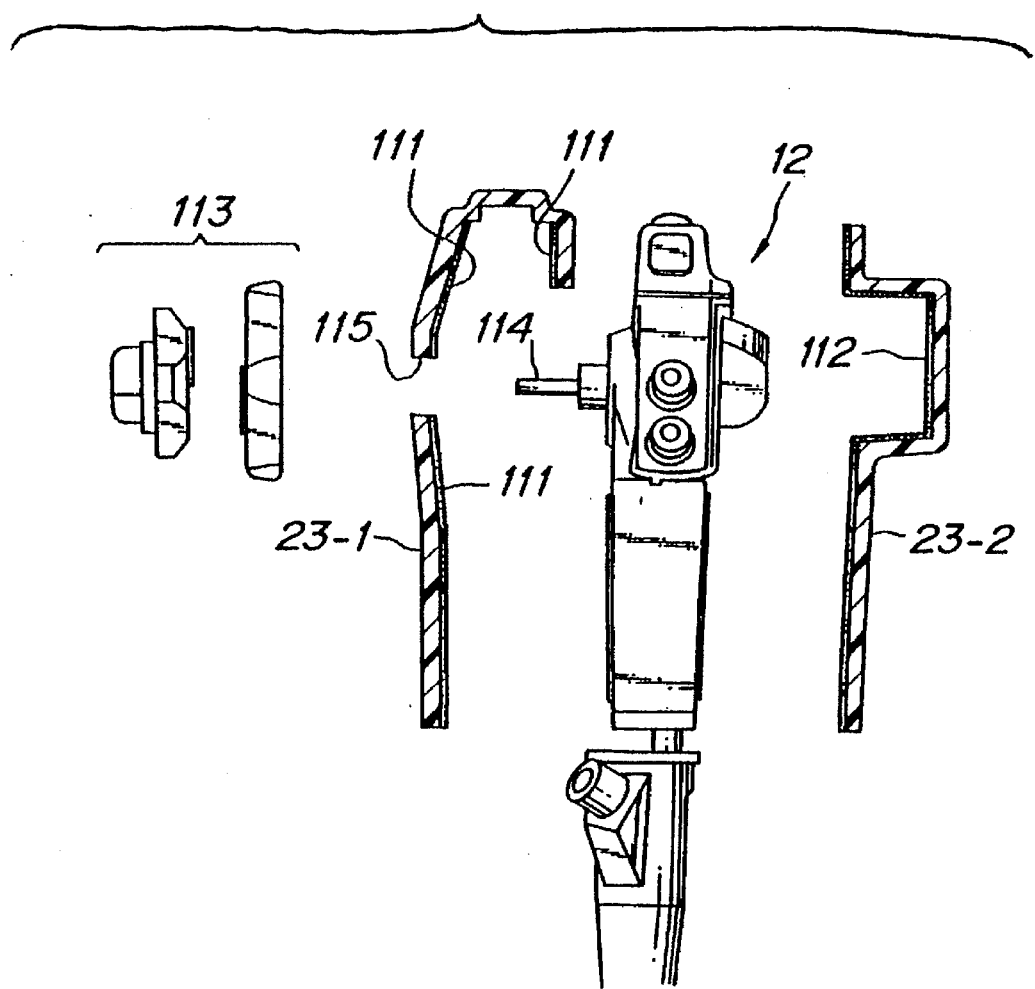
FIG. 12 is a partially cross sectional view showing another embodiment of the operation section cover according to the invention.

FIG. 12 shows another embodiment of the operation section cover for use in the endoscope system according to the invention. As explained above, in the endoscope system according to the invention, the shaft protrudes from the operation section cover via the aperture formed in the cover, and the angle knobs are detachably secured to the shaft. The diameter of the aperture formed in the operation section cover can be smaller than that of the angle knobs, and therefore the operation section of the endoscope is protected from contamination via the aperture. However, there is still a risk that the operation section is contaminated through the aperture. Further, the operation for covering the operation section with the disposable protection cover is somewhat difficult. In the present embodiment, the operation section cover is constituted by two cover halves 23-1 and 23-2, inner walls of these halves 23-1 and 23-2 except for portions corresponding to the control members, are coated with adhesive agents 111 and 112. For instance, a double-face adhesive tape or sheet may be applied on the inner walls of the operation section cover halves 23-1 and 23-2. By applying such adhesive agents 111 and 112, the cover halves 23-1 and 23-2 can be provided on the operation section 12 in an easy and accurate manner. Therefore, contamination via an aperture 115 formed in the cover half 23-1 can be effectively prevented and further a shaft 114 to which angle knobs 113 are detachably secured can be correctly protruded from the opening 115. Moreover, after the examination when the operation section cover halves 23-1 and 23-2 are removed from the operation section, the adhesive agents 111 and 112 are stuck together, so that the cover halves 23-1, 23-2 which have been once used can not be erroneously utilized again.

Figure 13:
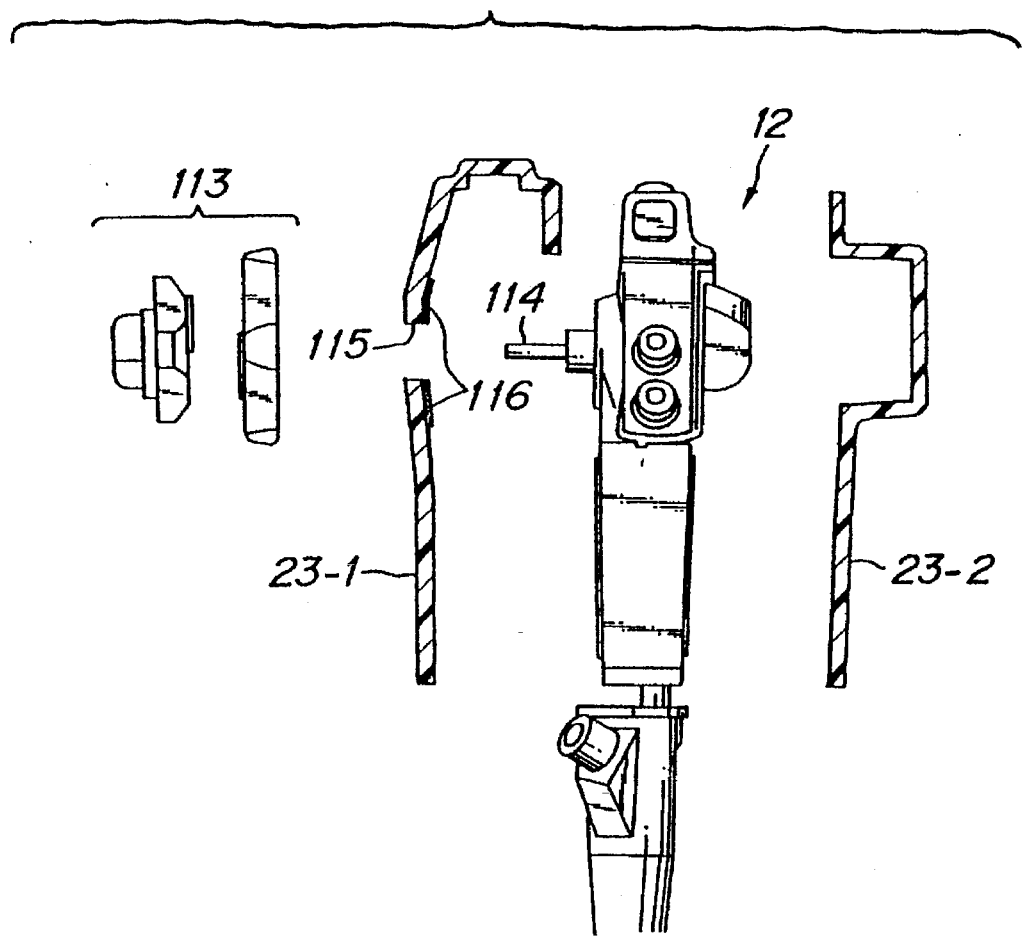
FIG. 13 is a partially cross sectional view illustrating still another embodiment of the operation section cover according to the invention.

FIG. 13 illustrates still another embodiment of the operation section cover for use in the endoscope system according to the invention. In the present embodiment, instead of applying the adhesive agents onto substantially the whole inner walls of cover halves 23-1 and 23-2, adhesive agent 116 is applied on the inner wall of the cover half 23-1 at a portion surrounding the aperture 115. Also in the present embodiment, contamination via the aperture 115 can be effectively prevented, and the position of the opening 115 is not deviated during the usage.

As explained above in detail, in the endoscope system according to the present invention, the shaft and angle knobs are constructed such that all angle knobs can be used commonly for all operation sections of various endoscopes. Therefore it is no longer necessary to select desired angle knobs, and damage to the angle knobs and shafts can be effectively prevented.

According to the second aspect of the present invention, the disposable protection cover for use with the endoscope is constructed such that the conduit channels are constructed such that the movement of the conduit channels in the radial direction within the insertion section cover is prevented over the whole length thereof. In such a disposable protection cover, the conduit channels are not freely moved in the radial direction over its whole length. Thus, the conduit channels can not prevent the smooth movement of the distal end of the endoscope, and the distal end can be directed into any desired direction during the examination. Now several embodiments of such protection cover according to the invention will be explained.

FIG. 14 is a cross sectional view of a middle portion of the insertion section 11 of the endoscope and the insertion section cover 22 of the embodiment shown in FIGS. 1 to 9. In the present embodiment, the air supply conduit channel 50, water supply conduit channel 51 and suction conduit channel (forceps channel) 52 have inner spaces whose cross section is circular, but their outer cross sectional configuration is not circular. That is to say, the three conduit channels 50, 51 and 52 are arranged side by side and an assembly of these conduit channels has a semicircular cross sectional outer configuration. Therefore, these conduit channels 50 to 52 can not be freely moved in the radial direction within the cover tube 45.

The remaining semicircular cross sectional space within the cover tube 45 forms the insertion section inserting channel into which the insertion section 11 of the endoscope is inserted. In the cross section of the insertion section 11 of the endoscope, there are provided the rubber tube 59, a pair of light guide optical fiber bundles 39, four signal conductors 48 connected to the solid state image sensor and enclosed by a rubber tube 151, and operating wires 57, 58. The wires 57 and 58 are separated from other components by partitions 152 and 153.

According to the present invention, the conduit channels 50 to 52 are formed such that they can not be moved in the radial direction within the cover tube 45, so that they do not interfere with the insertion section of the endoscope which is inserted into the insertion section inserting channel 49. Thus, the bend portion 54 of the endoscope can be smoothly bent by operating the angle knobs 33 and the distal end of the insertion section can be directed toward any desired direction.

FIG. 15 is a cross section of another embodiment of the disposable protection cover 22 according to the invention. In the present embodiment, the conduit channels 50 to 52 have the same cross section as that of the embodiment illustrated in FIG. 14, but within the cover tube 45 there is formed a partition 45a which extends diagonally to divide the inner space of the cover tube 45 into two semicircular portions. In one of the semicircular spaces, the conduit channels 50 to 52 are inserted, and in the other semicircular space, the insertion section 11 of the endoscope is inserted. By providing the partition 45a, the interference between the conduit channels 50 to 52 and the insertion section 11 can be prevented much more positively.

FIG. 16 is a cross sectional view depicting still another embodiment of the disposable protection cover according to the invention. Similar to the embodiment shown in FIG. 15, in the present embodiment, the inner space of the cover tube 45 is divided into two semicircular spaces by the partition 45a, but in the present embodiment, the outer configuration of the conduit channels 50 to 52 is formed differently from the previous embodiments. By forming the conduit channels 50 to 52 in the manner illustrated in FIG. 16, the radial movement of these channels within the cover tube 45 can be prevented furthermore positively. Moreover, in the upper semicircular space within the cover tube 45, there are formed spaces. Thus, the resistance against the movement of the distal end of the insertion section is reduced, and a necessary force for operating the angle knobs 33 can be decreased.

In the embodiments so far explained, the lateral cross section of the insertion section 11 of the endoscope is semicircular, and in the distal end construction member 41 of the protection cover 22 there is formed a corresponding semicircular hole such that the front end of the insertion section 11 of the endoscope is inserted into the semicircular hole. In this manner, the insertion section 11 of the endoscope can be indexed at the given angular position. According to the invention, it is not always necessary to form the insertion section of the endoscope to have the semicircular cross section, but it may be formed to have a circular cross section.

FIG. 17 is a cross sectional view showing an embodiment of the insertion section of the endoscope according to the invention having a circular cross section. In the present embodiment, an insertion section 171 comprises a distal end construction member 172. At a front end of the distal end construction member 172 there is formed a projection 173 integrally therewith. An insertion section cover 174 comprises a distal end construction member 175. In this distal end construction member there is formed a circular hole 176, and a groove 177 is formed in an inner wall of the circular hole 176. Upon inserting the insertion section 171 of the endoscope into an insertion section inserting channel of the insertion section cover 174, the projection 173 formed on the distal end construction member 172 of the insertion section 171 is inserted into the groove 177 formed in the distal end construction member 175 of the insertion section cover 174, and therefore the angular position of the insertion section 171 of the endoscope can be always correctly indexed. The remaining construction of the present embodiment is the same as that of the first embodiment shown in FIGS. 1 to 9, and thus its detailed construction is dispensed with.

In the embodiment illustrated in FIGS. 1 to 9, the light guide optical fiber bundle 39 is extended from the distal end of the insertion section of the endoscope to the proximal end of the universal cord, but there is proposed a separate type endoscope in which the light guide optical fiber bundle is separated at a position of the operation section. In such an endoscope, an optical connector is provided for detachably coupling the light guide optical fiber bundle to the operation section of the endoscope. In this case, an opening may be formed in the operation section cover at the optical connector. However, then there is a possibility of contamination via such opening. In order to avoid such contamination, it is desired not to form the opening in the operation section cover.

FIG. 18 is a cross sectional view showing an embodiment of the protection cover according to the invention which is advantageously used for the above-mentioned separate type endoscope. A light guide 181 extending through an insertion section is terminated at an operation section 182 by means of a fitting 183. To this fitting 183 is detachably secured an optical connector 185 provided at an end of a light guide optical fiber bundle 184 which is coupled with the light source. In an inner wall of the connector 185 there is formed a female screw 186, and in an outer wall of the fitting 183 there is formed a male screw 187 which is screwed to the female screw 186.

When the operation section 182 of the endoscope is covered with an operation section cover 188, it is no longer impossible to couple the connector 185 with the fitting 183. In the present embodiment the operation section cover 188 comprises a connecting member 189 at a position corresponding to the fitting 183. The connecting member 189 includes a base portion having a hole into which the fitting 183 can be inserted, a connecting window 190 and a male screw 191 which is screwed with the female screw 186 formed in the connector 185. Therefore, after the operation section cover 188 is provided on the operation section 182 of the endoscope, when the connector 185 is coupled with the connecting member 189, the light guide optical fiber bundles 181 and 184 can be optically connected with each other. In the present embodiment, the operation section cover 188 has no opening for the optical coupling, and therefore contamination via the opening can be prevented.

FIG. 19 is a side view showing an embodiment of the disposable protection cover according to the invention. After the endoscope has been covered with the disposable protection cover, the operation section of the endoscope is usually grasped by a left hand of a doctor, and the operation members such as the angle knobs are operated by the right hand of the doctor. When it is necessary to support the insertion section, the doctor grasps it with the right hand. Therefore, the right hand of the doctor might be a contamination source. In order to prevent the operation section of the endoscope from being contaminated by the right hand of the doctor, in the previous embodiments the operation section of the endoscope is covered with the disposable protection cover. In the present embodiment shown in FIG. 19, the operation section cover may be omitted.

As illustrated in FIG. 19, there is provided a ring 196 around an insertion section cover 195 movably along the insertion section cover, and a holding member 198 in the form of the right hand glove is secured to the ring 196 by means of a strap 197. During the examination, when it is necessary to grasp the insertion section, the doctor draws the right hand glove 198. When the angle knobs of the operation section are to be handled, the doctor takes off the right hand glove 198. In this manner, the contamination of the operation section of the endoscope can be effectively prevented without using the operation section cover.

As has been explained, the present invention also provides a novel insertion section cover in which the pin hole detection can be performed easily. Now several embodiments of such an insertion section cover will be explained.

Figure 20:
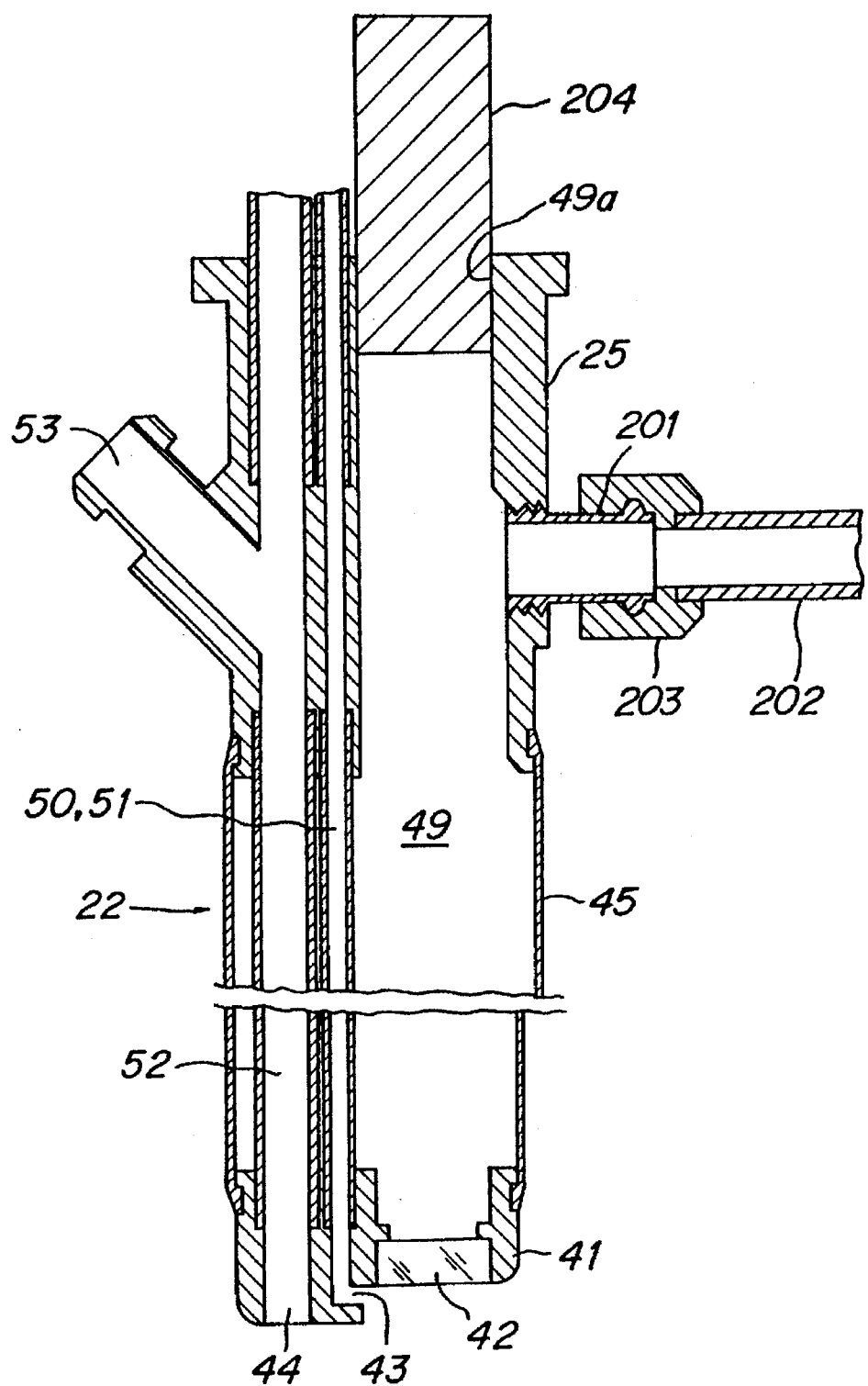
FIG. 20 is a cross sectional view showing another embodiment of the insertion section cover according to the invention.

FIG. 20 is a cross sectional view of an embodiment of the insertion section cover according to the invention. In the present embodiment, similar portions are denoted by the same reference numerals used in the previous embodiments. In the present embodiment, the pin hole detection is carried out by utilizing a nipple portion 201 which is used for inflating the insertion section cover when the insertion section of the endoscope is inserted into and removed from the cover. That is to say, the nipple portion 201 is provided in a connecting portion 25 of an insertion section cover 22. At a front end of a pin hole checking tube 202 there is arranged a coupling member 203 which is coupled with the nipple portion 201 in an air tight manner. The pin hole checking tube 202 is connected to a fluid supply source, in the present embodiment, an air supply device. There is further provided a plug 204 made of elastic material such as rubber. The plug 204 is inserted into an opening 49a through which the insertion section of endoscope is inserted into the insertion section inserting channel 49.

Figure 21:
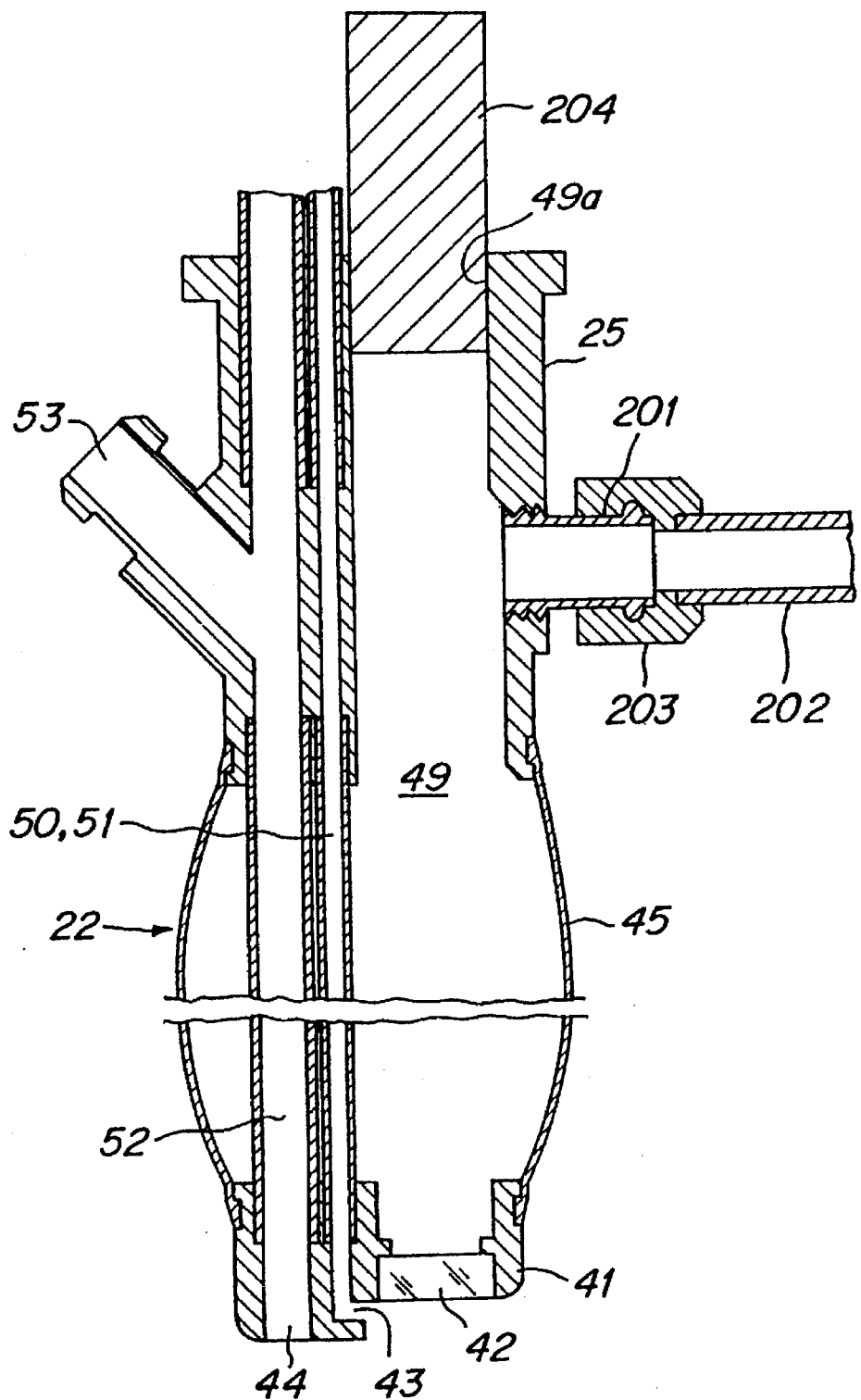
FIG. 21 is a cross sectional view representing the insertion section cover shown in FIG. 20 during the pin hole check operation.

FIG. 21 shows a condition in which after the opening 49a of the channel 49 has been closed by the plug 204, the air is supplied into the channel 49 by means of the pin hole checking tube 202 to inflate the cover tube 45 of the insertion section cover 22. If a pin hole is formed in the cover tube 45, the air is leaked out of the cover tube through the pin hole, so that the existence of the pin hole can be easily detected by checking this air leakage. This may be simply performed by observing the inflated condition of the cover tube 45 or by listening for an air leak noise.

Figure 22:
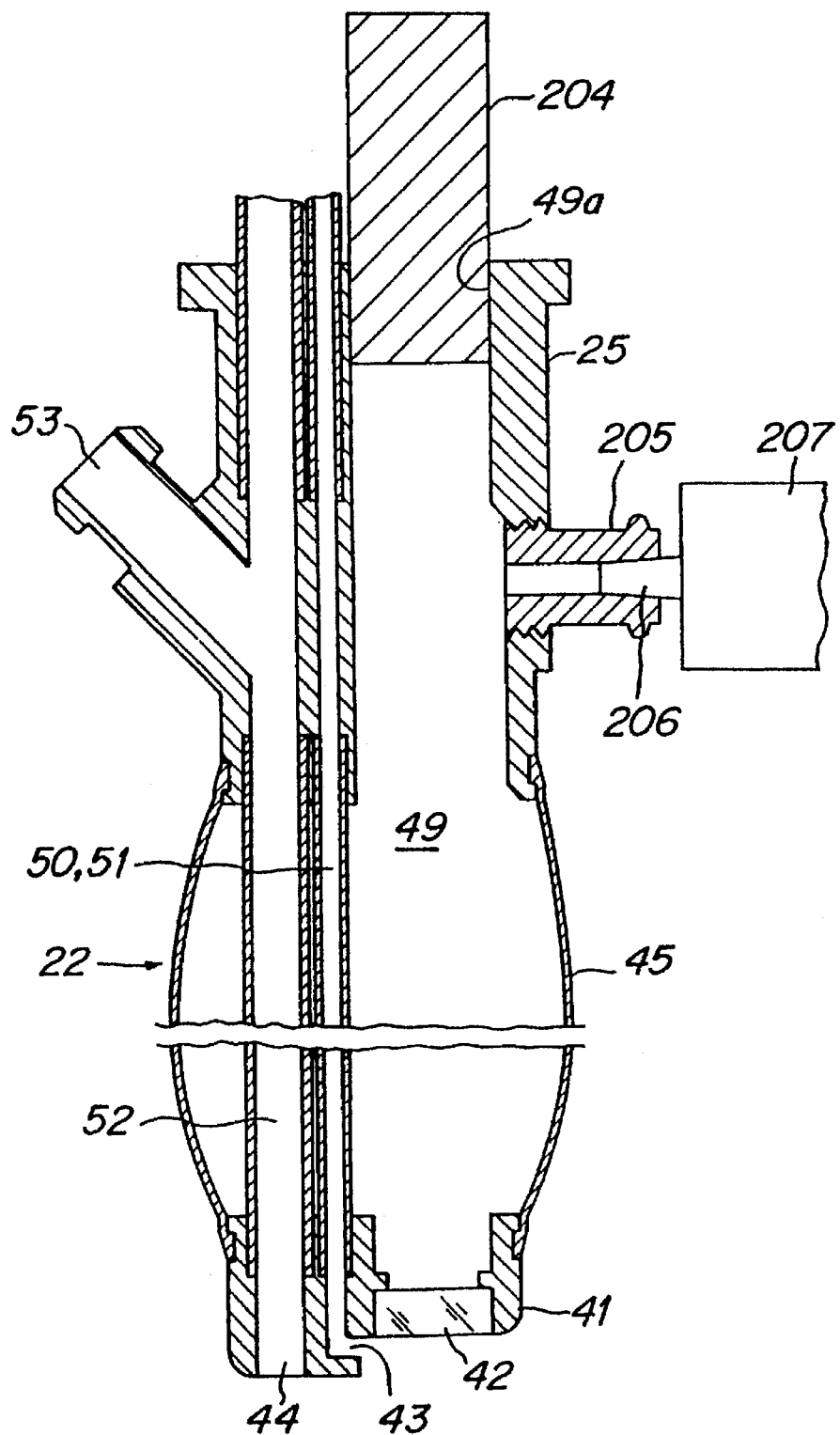
FIG. 22 is a cross sectional view showing another embodiment of the insertion section cover according to the invention.

FIG. 22 is a cross sectional view depicting another embodiment of the insertion section cover according to the invention in which the pin hole check can be carried out easily. In the embodiment shown in FIG. 21, the nipple portion 201 for inflating the cover tube 45 is constructed such that the coupling member 203 secured to the front end of the pin hole checking tube 202 is coupled with the nipple portion in an air tight manner, but in the present embodiment, a nipple portion 205 is formed such that a tapered front tip portion 206 of a pin hole checking syringe 207 can be inserted into a hole of the nipple portion 205 in an air tight manner. Also in the present embodiment, the opening 49a of the insertion section inserting channel 49 is closed by the plug 204. By operating the air syringe 207, it is possible to inflate the cover tube 45 in the same manner as that shown in FIG. 21, and a pin hole can be checked easily.

In the present embodiment, upon checking the pin hole, the cover tube 45 is inflated by operating the air syringe 207, so that it is not necessary to provide a special air supply device for inflating the cover tube. This is particularly advantageous for performing the pin hole check in the factory, because in the factory there is not provided the inflator for inflating the insertion section cover upon inserting the insertion section of the endoscope into the insertion section cover.

Figure 23:
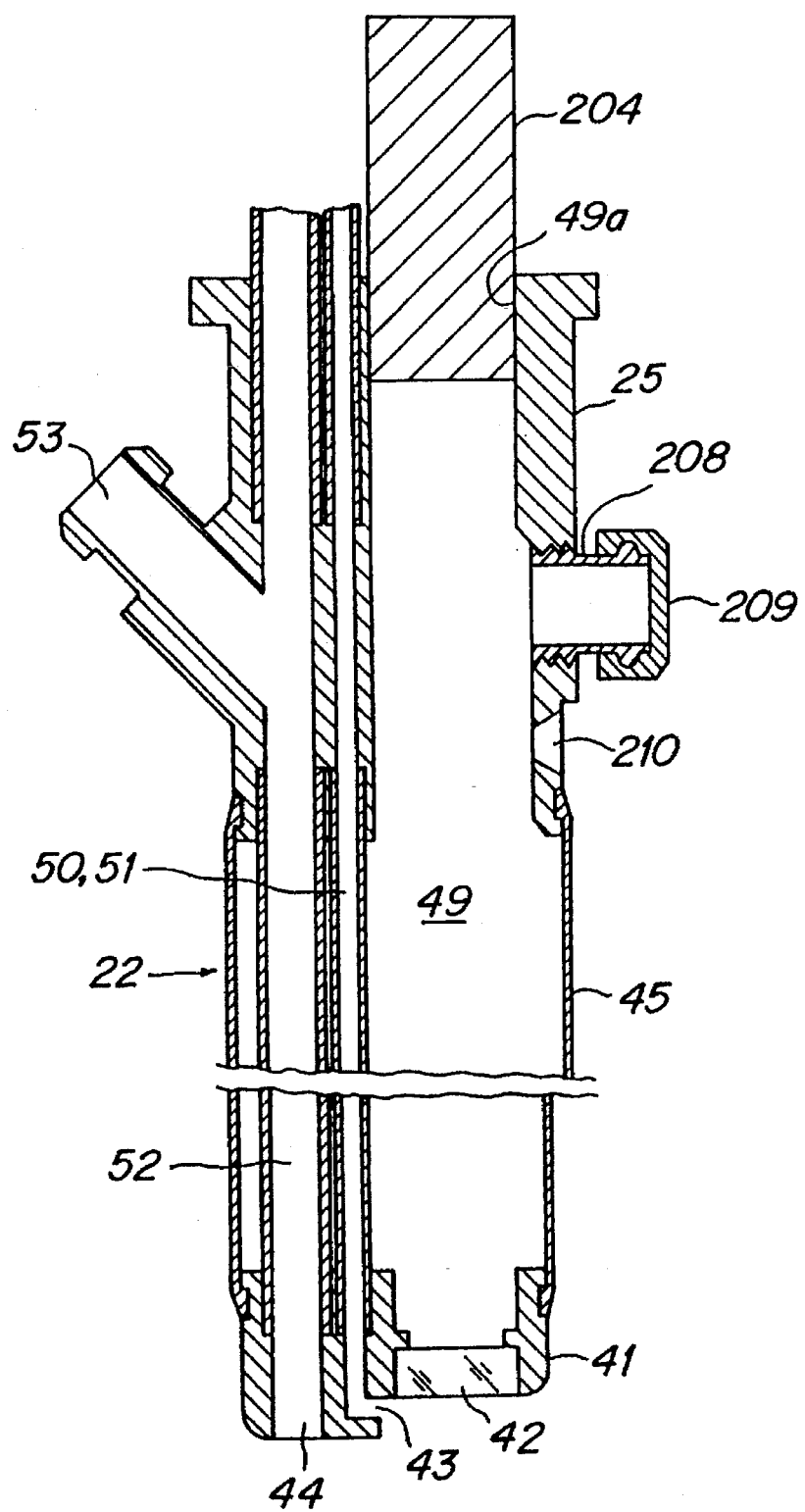
FIG. 23 is a cross sectional view illustrating still another embodiment of the insertion section cover according to the invention.

FIG. 23 shows still another embodiment of the protection cover according to the invention. In the embodiments shown in FIGS. 20 to 22, the nipple portion for inflating the cover tube upon inserting and removing the insertion section into and from the protection cover is utilized for the pin hole check. In the present embodiment, a nipple portion 208 is closed by a cap 209, and a pin hole check opening 210 is formed in the connecting portion 25 of the insertion section cover 22. The opening 49a of the insertion section inserting channel 49 is closed by the plug 204. In the present embodiment, a pin hole checking tube is inserted into the opening 210, and the cover tube is inflated to effect the pin hole check.

It should be noted that the present invention is not limited to the embodiments explained above, but many modifications and alternatives may be conceived by those skilled in the art within the scope of the invention. In the embodiments illustrated in FIGS. 1 to 13, there are provided two angle knobs, one for right and left movement and the other for up and down movement, but according to the invention it is sufficient to provide at least one angle knob. Further, in the embodiments shown in FIGS. 1 to 13, the disposable protection cover is constituted by the operation section cover, insertion section cover and universal cord cover, but according to the invention, the operation section cover and insertion section cover may be formed as a single integral unit, and the universal cord cover may be omitted. Moreover, in the embodiments illustrated in FIGS. 14 to 16, there are provided three conduit channels. However, according to the invention one or more conduit channels may be arranged within the insertion section cover. In the embodiments shown in FIGS. 20 to 23, the pin hole check is carried out by supplying air into the cover tube of the insertion section cover. But according to the invention, a special gas may be supplied into the cover tube, and a leakage of the gas may be detected by utilizing a chemical reaction. For instance, oxygen gas may be supplied into the cover tube, and the insertion section cover may be immersed into an alkali aqueous solution of pyrogallol.

What is claimed is:

1. An endoscope system comprising:

a first endoscope of image guide fiber bundle type having a housing of an operation section; an image guide optical fiber bundle extending within said housing; an eyepiece section, supported by said housing, for inspecting an image of an object which is transmitted by means of said image guide optical fiber bundle; a shaft extending from said housing; and at least one angle knob detachably secured to said shaft; and a second endoscope of solid state image sensing type having a housing of an operation section; a solid state image sensor, supported by said housing of said second endoscope, for converting an image of an object into an image signal; a switch section, supported by said housing of said second endoscope, for controlling the image picked up by said solid state image sensor; a shaft extending from said housing of said second endoscope; and at least one angle knob detachably secured to said shaft;

a first protection cover covering at least said housing of said first endoscope; and a second protection cover covering at least said housing of said second endoscope, wherein said angle knob and said shaft of said first endoscope and said shaft of said second endoscope are constructed such that said angle knob of the first endoscope can be detachably secured to said shaft of said second endoscope.

2. An endoscope system according to claim 1, wherein said shaft comprises first and second rotary shafts arranged coaxially with each other, a right and left angle knob is detachably secured to said first rotary shaft and an up and down angle knob is detachably secured to said second rotary shaft.

3. An endoscope system according to claim 2, wherein said disposable protection cover comprises an operation section cover for covering said operation section of the endoscope and an insertion section cover for covering said insertion section of the endoscope, and said aperture through which said shaft is protruded is formed in said operation section cover.

4. An endoscope system according to claim 3, wherein said operation section cover comprises first and second cover halves which are joined together to cover the operation section of the endoscope and said aperture through which said shaft is protruded is formed in said first cover half.

5. An endoscope system according to claim 4, wherein adhesive agents are applied on an inner wall of said disposable protection cover.

6. An endoscope system according to claim 4, wherein an adhesive agent is applied on an inner wall of said first cover half at a position which surrounds said aperture.

7. An endoscope system comprising:

an endoscope including an insertion section to be inserted into a cavity under inspection and an operation section to which a distal end of said insertion section is connected;

a protection cover including an insertion section cover which is constructed to cover said insertion section of the endoscope and has a first opening through which said insertion section of the endoscope is inserted into said insertion section cover;

a pin hole checking opening formed in said insertion section cover;

a means for supplying a fluid into said insertion section cover through said pin hole checking opening; and a plug-like member for being detachably inserted into said first opening formed in said insertion section cover such that a closed space is formed within said insertion section cover when said fluid is supplied into said insertion section cover.

* * * * *